Aug. 30, 1938. M. H. HORVATH Plant Pat. 288
ROSE
Filed Sept. 1, 1937
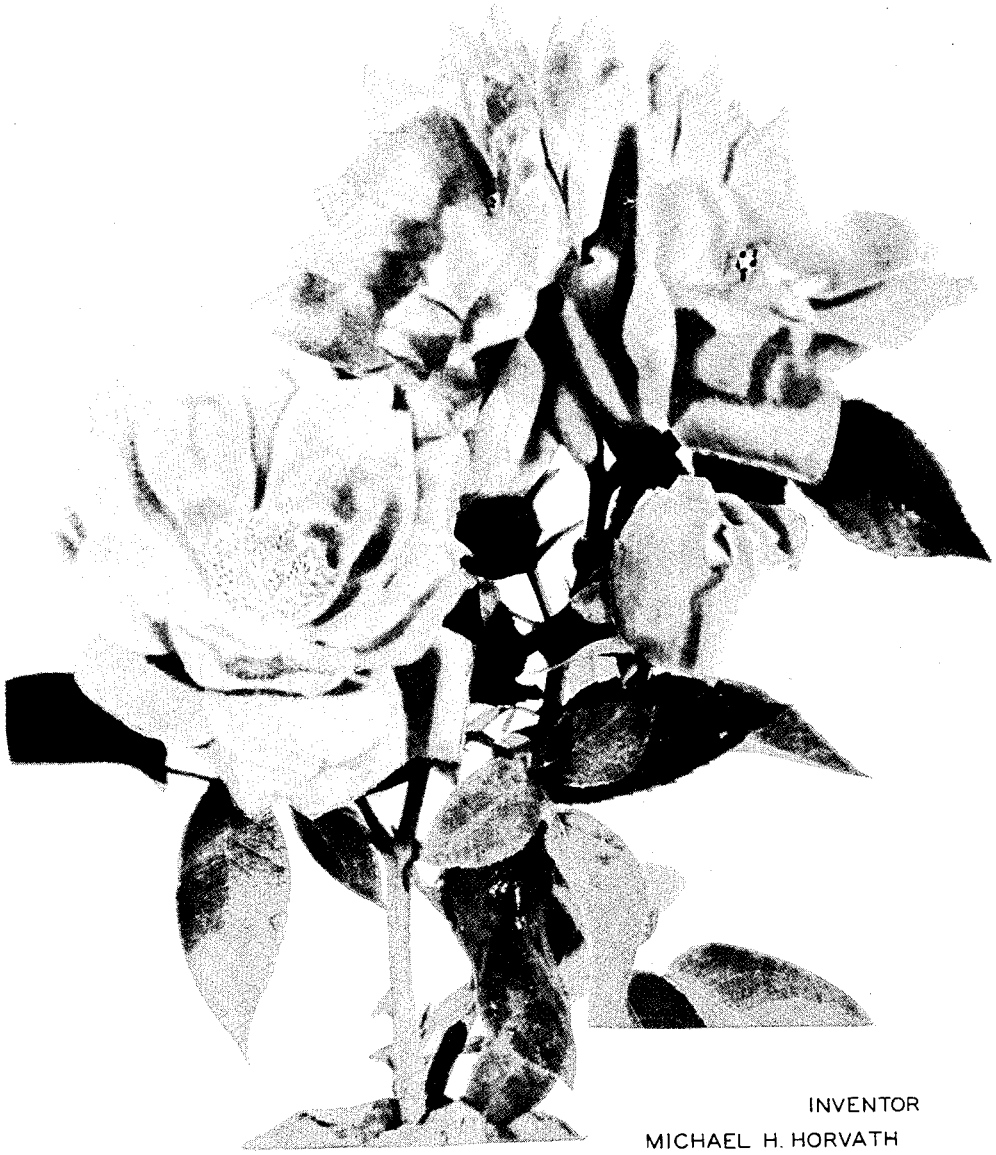
INVENTOR
MICHAEL H. HORVATH
BY John H. Brown,
HIS ATTORNEY Patented Aug. 30, 1938

Plant Pat. 288

UNITED STATES PATENT OFFICE

288

ROSE

Michael H. Horvath, Mentor, Ohio

Application September 1, 1937, Serial No. 162,062

1 Claim. (Cl. 47—61)

This invention relates to a novel and distinct rose, a "Rosa Setigera Hybrid", produced by crossing a rose variety "Papoose", as the female parent, with a rose variety "Paul Scarlet Climber", as the male parent. Successful asexual reproduction has been made.

This new rose is distinctly a hardy variety. It grows without protection in the temperate region, and it can be successfully grown with protection in the colder regions where the growing of roses has been impossible or exceedingly difficult.

The shrub grows to a height of thirty inches or more, with a spread of or exceeding four feet. The stems and stalks are glabrous and of a sturdy character both in appearance and in supporting the clusters of flowers and foliage. The foliage is of a deep rich green color, corresponding to Maerz and Paul Plate No. 24 L—5, and it grows in amount so as to greatly accent the beauty of the rose.

The flowers are an attractive and distinctive cerise, Plate No. 4 J—6, with a pronounced light yellow center, Plate No. 10 H—4, spotted with stamens bearing tops of darker color in contrast. Each flower has some twenty-six to twenty-eight petals.

The drawing further illustrates many of the characteristics which are not found in the parent stock or known rose varieties, but which add to the value of the plant as a shrub and increase its beauty, such as the pointed shape of the bud, sturdy appearing stems, shape and size of bloom, light texture and shape of petals and oval-shaped leaflets having serrated edges and of a glabrous texture with inconspicuous ribs and veins.

Having now fully shown and described my new rose and the mode of its production, what I claim and desire to secure by Letters Patent of the United States is:

A rose as herein shown and described and distinguished by its hardy and sturdy characteristics, its shrub growth and appearance, its deep rich green foliage abundantly produced, and its cluster-borne cerise flowers with a center of pronounced light yellow.

MICHAEL H. HORVATH.